United States Patent
Roedle

(10) Patent No.: US 11,160,930 B2
(45) Date of Patent: Nov. 2, 2021

(54) MEDICATION DEVICE

(71) Applicant: VETTER PHARMA-FERTIGUNG GMBH & CO. KG, Ravensburg (DE)

(72) Inventor: Tilman Roedle, Wolfegg (DE)

(73) Assignee: VETTER PHARMA-FERTIGUNG GMBH & CO. KG, Ravensburg (DE)

( * ) Notice: Subject to any disclaimer, the term of this patent is extended or adjusted under 35 U.S.C. 154(b) by 160 days.

(21) Appl. No.: 16/364,344

(22) Filed: Mar. 26, 2019

(65) Prior Publication Data

US 2019/0217011 A1 Jul. 18, 2019

Related U.S. Application Data

(63) Continuation of application No. 15/524,686, filed as application No. PCT/EP2015/077069 on Nov. 19, 2015, now abandoned.

(30) Foreign Application Priority Data

Nov. 20, 2014 (DE) ...................... 10 2014 223 693.2

(51) Int. Cl.
*A61M 5/24* (2006.01)
*A61J 1/06* (2006.01)
(Continued)

(52) U.S. Cl.
CPC .............. *A61M 5/24* (2013.01); *A61J 1/065* (2013.01); *A61M 5/28* (2013.01); *A61M 5/3129* (2013.01);
(Continued)

(58) Field of Classification Search
CPC .................. A61M 5/24; A61M 5/3129; A61M 2005/2403; A61M 2205/0238;
(Continued)

(56) References Cited

U.S. PATENT DOCUMENTS 5,810,001 A 9/1998 Genga et al.
6,640,138 B1 10/2003 Schaefermeyer et al.
(Continued)

FOREIGN PATENT DOCUMENTS

| DE | 102004036358 A1 | 2/2006 |
| DE | 60113440 T2 | 6/2006 |
| WO | 2009140782 A1 | 11/2009 |

OTHER PUBLICATIONS

Office Action to corresponding Japanese application 2017-526933 dated Jun. 11, 2019.
(Continued)

*Primary Examiner* — Shefali D Patel
(74) *Attorney, Agent, or Firm* — Harness, Dickey & Pierce, P.L.C.; Stephen T. Olson

(57) ABSTRACT

A medication device with a cartridge or a syringe having a longitudinal axis and containing a medicament, a housing receiving the cartridge or the syringe and having a center axis, and with an RFID device comprising at least one RFID chip with a first antenna, at least one RFID readout unit with a second antenna, wherein the at least one RFID chip is associated with the cartridge or the syringe or the housing and the at least one RFID readout unit is associated accordingly with the housing or the cartridge or the syringe. The first antenna of the at least one RFID chip and the second antenna of the at least one RFID readout unit are each embodied as a coil and aligned so as to be coaxial with one another and with the longitudinal axis as well as with the center axis.

23 Claims, 5 Drawing Sheets

(51) Int. Cl.
*A61M 5/28* (2006.01)
*A61M 5/31* (2006.01)
*A61M 5/145* (2006.01)
*A61M 5/19* (2006.01)

(52) U.S. Cl.
CPC ......... *A61J 2205/60* (2013.01); *A61M 5/1452* (2013.01); *A61M 5/19* (2013.01); *A61M 5/2448* (2013.01); *A61M 2005/2403* (2013.01); *A61M 2205/3592* (2013.01); *A61M 2205/6054* (2013.01); *A61M 2207/00* (2013.01)

(58) Field of Classification Search
CPC ...... A61M 2205/19; A61M 2205/3592; A61M 2205/6054; A61M 5/28; A61M 2205/60; A61M 2207/00; A61J 2205/60; A61J 1/065
See application file for complete search history.

(56) References Cited

U.S. PATENT DOCUMENTS

| | | |
|---|---|---|
| 2003/0052788 A1 | 3/2003 | Chung |
| 2007/0225653 A1 | 9/2007 | Lim et al. |
| 2009/0149744 A1* | 6/2009 | Nemoto ................ A61M 5/172 600/432 |
| 2010/0305506 A1 | 12/2010 | Fahrer |
| 2011/0152825 A1 | 6/2011 | Marggi |
| 2012/0078181 A1 | 3/2012 | Smith et al. |
| 2013/0146613 A1* | 6/2013 | Balthes .................... G05B 9/00 604/189 |
| 2016/0166471 A1* | 6/2016 | Tobescu ................... A61J 1/18 340/691.6 |

OTHER PUBLICATIONS

International Search Report for PCT/EP2015/077069, ISA/EP, Rijswijk, NL, dated Feb. 29, 2016, with English translation.
Written Opinion of the ISA for PCT/EP2015/077069, ISA/EP, Rijswijk, NL, dated Feb. 29, 2016.
International Preliminary Report on Patentability (Ch.I) for PCT/EP2015/077069, IB, Geneva, dated May 23, 2017, incorporating the English Translation of the Written Opinion of the ISA.

* cited by examiner

MEDICATION DEVICE

CROSS-REFERENCE TO RELATED APPLICATIONS

This application claims priority to U.S. application Ser. No. 15/524,686 filed 5 May 2017 which is a 371 U.S. National Stage of International Application No. PCT/EP2015/077069 filed 19 Nov. 2015, which claims the benefit of and priority to German Application No. 10 2014 223 693.2 filed on 20 Nov. 2014. The disclosures of the above applications are incorporated herein by reference.

FIELD

The invention relates to a medication device with a cartridge or a syringe.

BACKGROUND

Medication devices with a cartridge or syringe, an associated housing and an RFID (Radio Frequency Identification) device are known. They are characterized in that they can be used to obtain information about a cartridge or syringe inserted into a housing and, for example, about the contents thereof. It was found that, in many cases, the signal transmission between the RFID chip and the RFID readout unit is not satisfactory, so the desired information is often not accessible.

SUMMARY

It is therefore the object of the invention to provide a medication device of the abovementioned type in which increased functional reliability is ensured.

To achieve this object, a medication device is proposed which has the features named in claim 1. Accordingly, the medication device has a cartridge or syringe with an associated housing which comprise a longitudinal or center axis, as well as an RFID device with a chip and a readout unit. The chip of the cartridge or syringe and the readout unit are associated with the housing or vice versa. Both the chip and the readout unit are provided with an antenna.

The medication device is characterized in that each of the antennas is embodied as a coil and aligned such that they are coaxial with one another and with the longitudinal axis of the cartridge and with the center axis of the housing. This arrangement of the antennas of the RFID device ensures that an optimal signal transmission occurs from the chip to the readout unit, thus enabling secure information transfer—particularly independently of a relative rotational position of the cartridge to the housing.

In a preferred exemplary embodiment of the medication device, a provision is made that the first antenna of the RFID chip and/or the second antenna of the RFID readout unit can be mounted on the cartridge or housing by means of a shrinkable sleeve. This makes it possible in a simple manner to arrange the antennas exactly in a desired position and then to easily fasten them in place.

In another preferred exemplary embodiment, a provision is made that the coil of the first and/or second antenna is embodied as a closed ring or as a ring segment or as a spiral. It is possible to embody the two antennas of the RFID chip and RFID readout unit differently.

Additional embodiments follow from the subclaims.

DESCRIPTION OF THE DRAWINGS

The invention is explained below in further detail with reference to the drawings.

DETAILED DESCRIPTION

Figure 1:
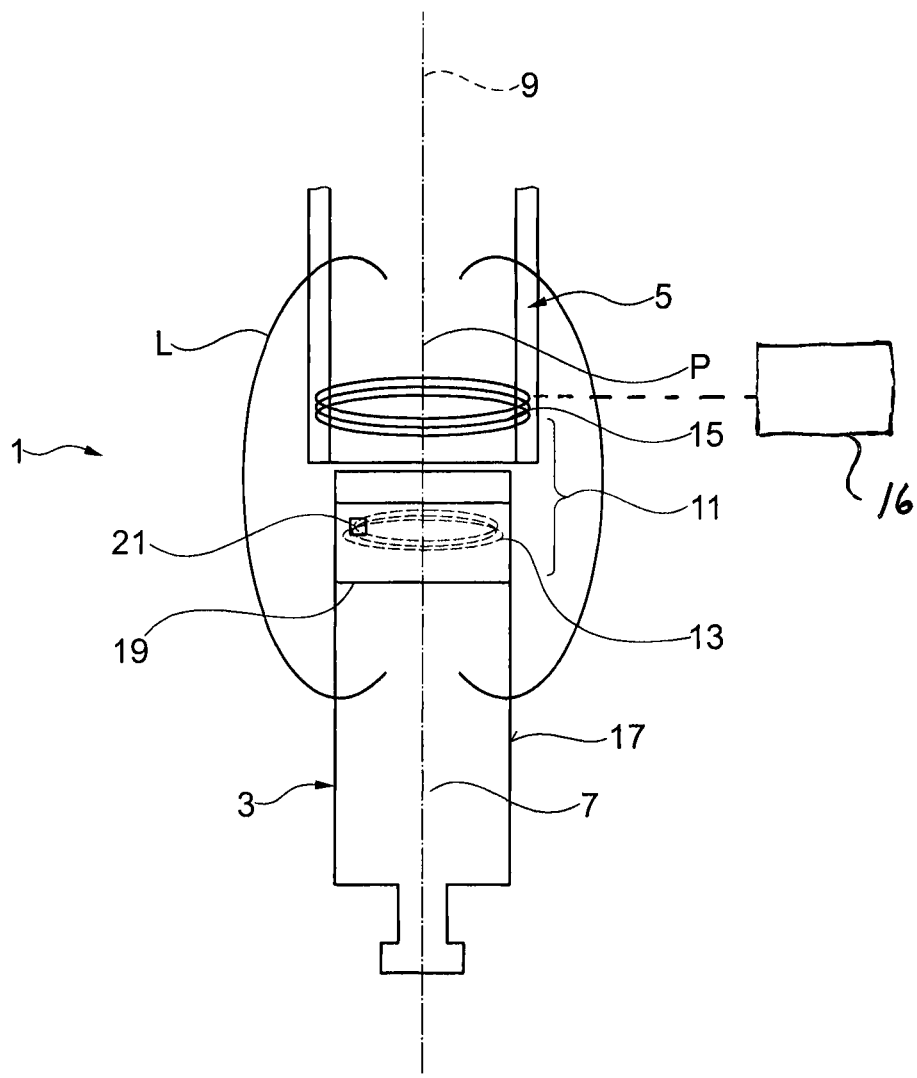
FIG. 1 shows a schematic diagram of a medication device with a cartridge and a housing, both of which are provided with an antenna.
Figure 5:
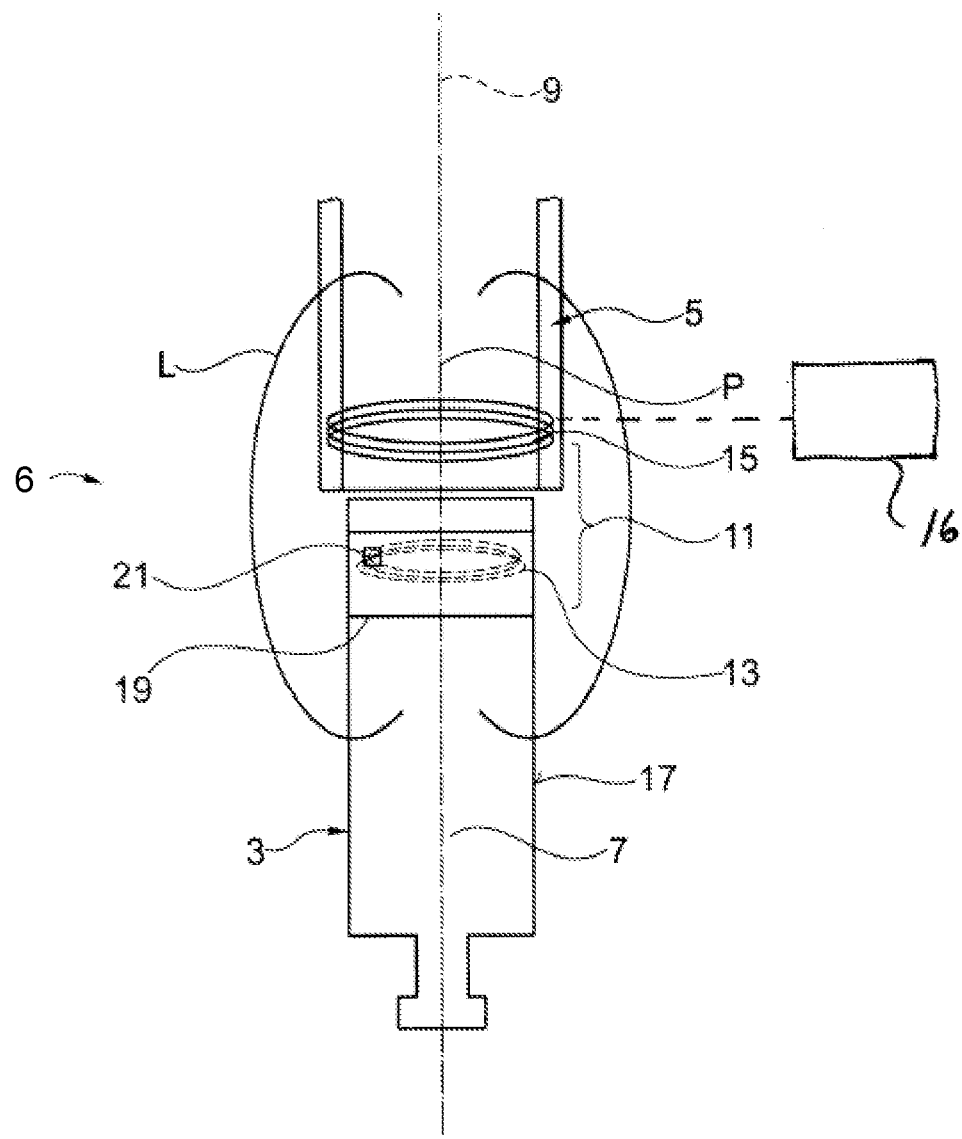
FIG. 5 shows a schematic diagram of a pen with a cartridge and a housing, both of which are provided with an antenna.

FIG. 1 shows a schematic diagram of a medication device 1, which comprises a cartridge 3 as well as a housing 5, which is broken away here. The medication device 1 can be a pen 6 as shown in FIG. 5, for example, that is used to administer a medicament that is located within the cartridge 3.

According to FIG. 1, the cartridge 3 has a longitudinal axis 7, and the housing 5 a center axis 9. It can be seen that these two axes are coaxial, i.e., coincident, with one another.

The medication device 1 has an RFID device 11 with a first antenna 13 and a second antenna 15. Both of these are embodied as coils. For the sake of example, a provision is made that the first antenna 13 is helical, whereas the second antenna 15 is annular, particularly spiral-shaped. This design of the antennas is selected in such a way that is advantageous for the mounting of the antennas.

In FIG. 1, the first antenna 13 is helical because it can thus be optimally mounted on the outer surface of the cartridge 3. In this case, it is possible to fasten or design the first antenna 13 on the outer surface 17 in any desired manner. What is more, it is conceivable for the first antenna to be integrated into the wall of the cartridge 3. It is thus possible to print, glue, or—as is preferably the case here—fasten an antenna by means of a shrinkable sleeve 19 to the outer surface 17. This will be discussed below in greater detail.

The first antenna 13 is coupled with an RFID chip, whereas the second antenna 15 is coupled with an RFID readout unit 16 (shown in simplified form in FIG. 1).

The second antenna 15 is embodied here as a spiral for the sake of example. It is certainly possible for this second antenna 15 to also be helical and provided on the outside on the wall of the housing 5 or on the inner side thereof, or for it to be integrated into the wall of the housing 5.

In the exemplary embodiment of the medication device 1 illustrated here, two differently designed antennas are thus combined with one another, with the first antenna 13 being associated with the cartridge 3 and the second antenna 15 being associated with the housing 5.

It is clear from FIG. 1 that the first antenna 13 is arranged helically around an imaginary axis that coincides with the longitudinal axis 7 of the cartridge 3. Moreover, a provision is made that the second antenna 15 extends around an imaginary axis that coincides with the center axis 9 of the housing 5. Finally, it can be seen that the axes of the two antennas 13 and 15 as well as the longitudinal axis 7 of the cartridge 3 and the center axis 9 of the housing 5 coincide, that is, are coaxial with one another.

It can be seen from FIG. 1 that the fields of the first and second antenna 13 and 15 run coaxially with the longitudinal axis 7 of the cartridge 3 and the center axis 9 of the housing 5, as is shown clearly by an arrow P extending coaxially with the longitudinal and center axis. The outer lines L indicate how the field formed by the antennas 13 and 15 extends outward.

In particular, it can be seen that the fields of the antennas 13 and 15 penetrate through one another coaxially, so that a relative rotation between cartridge 3 and housing 5 does not have any effect on the transfer of energy to the RFID chip 21 and the readout by the RFID readout unit of the data present on the RFID chip 21 is optimally ensured.

In FIG. 1, the antennas 13 and 15 are shown as closed coils. It is not necessary for the antennas to be embodied as closed rings. It is also conceivable for a ring segment to be used as an antenna.

Figure 2:
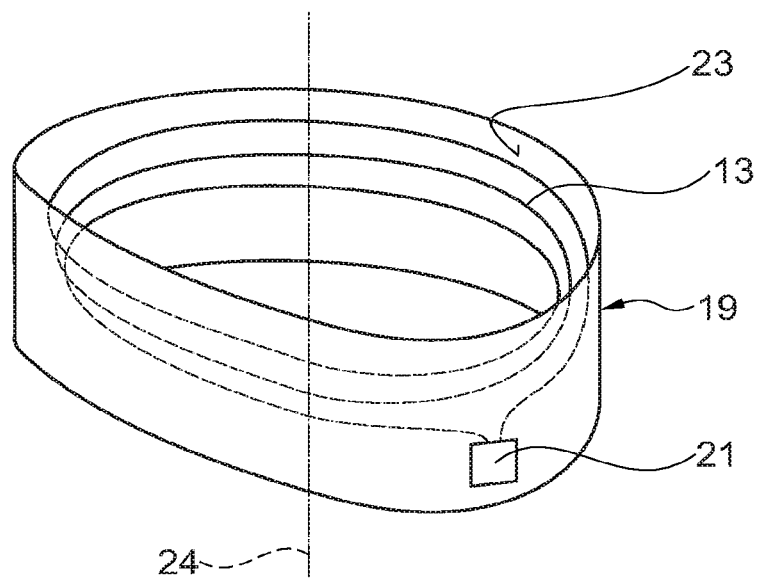
FIG. 2 shows a schematic diagram of an antenna with an RFID chip combined with a shrinkable sleeve.

FIG. 2 shows a portion of the medication device 1, namely in a schematic diagram of an antenna coupled with an RFID chip by a shrinkable sleeve. Same and functionally analogous elements are provided with the same reference symbols, so reference is made in that regard to the preceding description.

FIG. 2 shows the shrinkable sleeve 19 (visible in FIG. 1), which is provided with the first antenna 13, which is coupled with an RFID chip.

It is possible for the antenna 13 and the shrinkable sleeve 19 to be embodied separately and for the antenna 13 to be first placed on the outer surface 17 of a cartridge 3, for example, and then fixed in place with the shrinkable sleeve 19. Usually, a shrinkable sleeve 19 is selected which has a diameter that is greater than the outside diameter of the cartridge 3 or of the object, for example also of the housing 5 on which the antenna 13 is to be mounted. By virtue of the larger inside diameter, the shrinkable sleeve 19 is easy to put in position. It is then heated, for example, and its material is designed such that it shrinks as the temperature rises, so that the inside diameter of the shrinkable sleeve 19 decreases and it comes to rest firmly on the outer surface of the object on which the antenna is to be mounted.

It is also conceivable for the shrinkable sleeve 19 to be made of materials that shrink through the effect of chemicals or light, particularly UV light or the like.

Shrinkable sleeves are inherently known, so their design and functionality will not be discussed further.

Therefore, to summarize, FIG. 2 shows a shrinkable sleeve 19 on whose inner side 23 the first antenna 13 is mounted, glued, or placed, thus forming a unit of antenna 13 and shrinkable sleeve 19. What is more, it is conceivable for the first antenna 13 to be integrated into the wall of the shrinkable sleeve 19, preferably along with the RFID chip 21.

The shrinkable sleeve 19, and hence the first antenna 13 as well, extend around an axis 24.

It can be seen from FIG. 2 that the first antenna 13 is helical. It is certainly also conceivable to combine a helically-shaped antenna with the shrinkable sleeve 19, the windings of which lie on a plane on which the axis 24 stands perpendicularly.

The first antenna 13 and the second antenna 15 visible from FIG. 1 are embodied here as a helix or as an annular coil. It should be expressly noted here that both antennas 13 and 15 can also have two or more sub-antennas, which are preferably arranged so as to be coaxial with one another.

Figure 3:
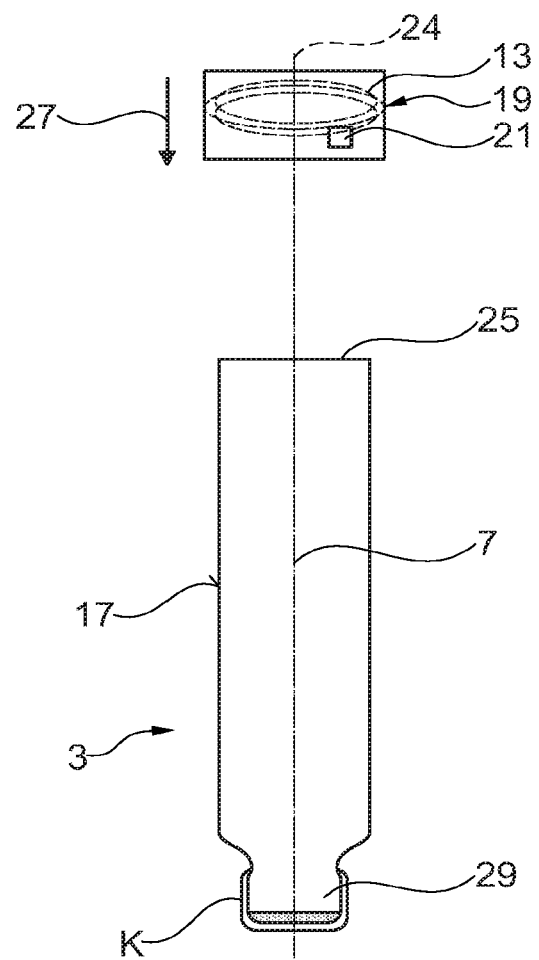
FIG. 3 shows a schematic, exploded view of a shrinkable sleeve according to FIG. 2 with a cartridge.

FIG. 3 shows a schematic, exploded view of a shrinkable sleeve according to FIG. 2 with a cartridge. Same and functionally analogous elements are provided with the same reference symbols, so reference is made in that regard to the preceding description.

It can be seen from FIG. 3 that the shrinkable sleeve 19 with the antenna 13 having an RFID chip 21 is designed to be so large in the initial state—i.e., has such an inside diameter—that it can be pushed without difficulty over a cartridge 3. It can be displaced readily over the outer surface 17 of the cartridge 3 and positioned in a desired position. Preferably, it is arranged in the proximity of the upper edge 25 of the cartridge 3, as can be seen from FIG. 1.

After placement of the shrinkable sleeve 19 onto the outer surface 17 of the cartridge 3 in the direction of the arrow 27, a shrinking procedure involving the shrinkable sleeve 19 is initiated, so that the shrinkable sleeve 19 comes to rest firmly on the outer surface 17 and is held in a desired position. The RFID chip 21 is also fixed to the cartridge 3, thus preventing damage, particularly to the connection between RFID chip and antenna.

The shrinkable sleeve 19 is arranged so as to be coaxial with the cartridge 3, so that the axis 24 of the shrinkable sleeve 19 and the longitudinal axis 7 of the cartridge 3 are coaxial with one another and coincide.

The cartridge 3 can be embodied as a conventional single-chamber cartridge or as a known dual-chamber cartridge. Its outside diameter is selected such that it can be inserted readily into the interior of the housing 7. It can be connected at its end 29 opposite the edge 25 to a cannula or to another injection system in order to enable administration of the medicament contained in its interior to a patient.

The cartridge 3 can be sealed at its lower end in any known manner, for example by a cap K, as is indicated in FIG. 3.

Figure 4:
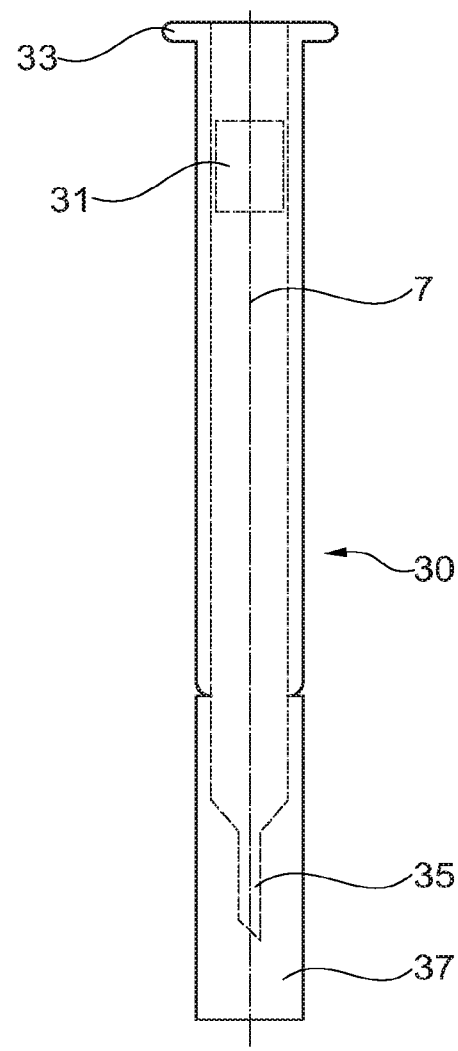
FIG. 4 shows a schematic, exploded view of a medication device with a syringe with an antenna.
Figure 4:
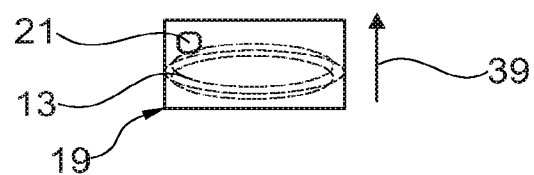

FIG. 4 shows a schematic view of a medication device having a syringe with an antenna. Same and functionally analogous elements are provided with the same reference symbols, so reference is made in that regard to the preceding description.

The exemplary embodiment illustrated in FIG. 4 differs from the embodiment shown in FIGS. 1 and 3 in that, instead of a cartridge, a syringe 30 is used here which is embodied as a single-chamber syringe in FIG. 4 for the sake of example. As will readily be understood, it is also possible to use dual-chamber syringes in conjunction with the medication device described herein.

The syringe 30 shown here is combined with a housing 5 of a medication device 1, as was explained with reference to FIG. 1. The syringe 30 has a longitudinal axis 7 that is coaxial with the housing 5 (not shown here) of a medication device 1.

For the sake of example, the syringe 30 has at least one stopper 31 here that can be displaced within the syringe along its longitudinal axis 7. At its end facing toward the housing 5 of the medication device 1, it also has a circumferential projection 33 and, at its opposing end, a cannula 35. The latter can also be placed later onto the syringe 30 before use. In the exemplary embodiment shown here, a protective cap 37 is provided on the end opposite the projection 33 which covers the cannula 35.

Syringes 30 of the type referred to here are known and can have various designs. In relation to the medication device being discussed here, the specific design of the syringe 30 is not important.

What is crucial is that the syringe 30 have a first antenna 13 as is also the case with the cartridge 3 of the first exemplary embodiment of the medication device 1. The first antenna 13 provided on the syringe 30 is also helical here and connected to an RFID chip 21.

An arrow 39 indicates here that the first antenna 13 or a shrinkable sleeve 19 can be pushed from below—i.e., from the end of the syringe 30 opposite the projection 33—onto the base body of the syringe 30. As described with reference to the first exemplary embodiment, heat, light, or the like is then applied to the shrinkable sleeve, so that it shrinks onto the syringe 30.

In principle, it is certainly possible to mount the first antenna 13 directly on the base body of the syringe 30, whether by printing, gluing, or the like. Finally, it is also possible for the first antenna 13 to be integrated into the wall of the syringe 30, which receives the at least one stopper 31. The remarks made regarding the cartridge 3 apply here analogously.

It is simplest, however, if the first antenna 13 is pushed by means of a shrinkable sleeve 19 over the base body of the syringe 30 and then fastened there.

Regarding the design of the first antenna 13, the shrinkable sleeve 19, the integration of the first antenna 13 into the shrinkable sleeve 19, and the fastening thereof on the syringe 30, reference is otherwise made to the explanations concerning this aspect in the exemplary embodiment with the cartridge 3 in relation to FIGS. 1 to 3.

In conjunction with the medication device 1, a conventional RFID device is provided which, as pointed out above in relation to FIG. 1, has a known readout unit that cooperates with the second antenna 15.

The RFID readout unit usually comprises a power sources in order to feed power via the second antenna 15 and the first antenna 13 on the cartridge 3 or syringe 30 to the RFID chip 21 and to read out data after activation of the chip.

Given that the two antennas 13 and 15 are arranged so as to be coaxial with one another as well as with the housing 5 and the cartridge 3 or syringe 30, respectively, it is ensured that the power from the RFID readout unit is transferred optimally to the RFID chip 21. At the same time, it is ensured that data from the RFID chip 21 are transferred via both antennas 13 and 15 to the RFID readout unit.

Particularly, it is ensured in this way that the RFID chip 21 transfers information about the cartridge 3 or syringe 30 (for example, regarding their size or the like), about the medicament contained in the cartridge 3 or syringe 30, and/or about the route of administration for the medicament. The remaining volume of a medicament in the cartridge 3 or syringe 30 can also be transmitted to the RFID readout unit, for example.

Information about the medicament itself and the usual dosage or the dosage arranged for a patient can also be easily transmitted.

In view of the above, the following is clear:

What is crucial for the embodiment of the medication device 1 described here is that two antennas 13 and 15 of an RFID device 11 embodied as coils are aligned such that they are coaxial with one another and with the longitudinal axis 7 and center axis 9 of the medication device 1.

One of the antennas can be spiral-shaped or embodied as a ring segment, while the other is helical. A spiral-shaped or helical design of both antennas 13 and 15 is also possible.

What is essential is the coaxial arrangement of the antennas, so that power and—preferably in the opposite direction, data—can be optimally transferred from one to the other.

The antennas can be mounted on the wall of a cartridge 3 or syringe 30 and/or of a housing 5 and can be preferably fastened by means of a shrinkable sleeve 19. It is also conceivable, however, for one or both antennas to be provided on the inner side of the cartridge 3 or syringe 30 or housing 5, or to be integrated into the wall of the cartridge 3 or syringe and/or housing 5.

Preferably, the first antenna 13 is arranged on the outer surface 17 of the cartridge 3 or syringe 30, because this type of mounting is easy to execute and the interior space of the cartridge or syringe remains free. The inner wall of the cartridge or syringe in particular should remain free to the greatest possible extent, because at least one stopper or plunger is inserted into the interior thereof and should be able to be displaced freely and easily.

The invention claimed is:

1. A medication device comprising:
    a cartridge or a syringe having a longitudinal axis and containing a medicament;
    a housing receiving the cartridge or the syringe and having a center axis; and
    an RFID device including:
        at least one RFID chip with a first antenna,
        at least one RFID readout unit with a second antenna, the at least one RFID chip associated with one of the cartridge or the syringe and the housing and the at least one RFID readout unit associated with the other of the cartridge or the syringe and the housing, the first antenna of the at least one RFID chip and the second antenna of the at least one RFID readout unit each embodied as a coil independently extending completely around the longitudinal axis or the center axis and aligned so as to be coaxial with one another and with the longitudinal axis as well as with the center axis, and
        a shrinkable sleeve mounting at least one of the first antenna and the second antenna on an outer surface of an object selected from a group consisting of: (1) the cartridge or the syringe; and (2) the housing,
    wherein the shrinkable sleeve rests firmly against the outer surface of the object.

2. The medication device as set forth in claim 1, wherein the housing is a part of a pen by which the medicament contained in the cartridge or the syringe can be administered.

3. The medication device as set forth in claim 1, wherein the at least one RFID chip contains information about the medicament contained in the cartridge or the syringe and/or about a route of administration of the medicament.

4. The medication device as set forth in claim 1, wherein the medication device is a pen.

5. The medication device as set forth in claim 1, wherein the shrinkable sleeve has been subjected to heat, light, or a chemical so that an inside diameter of the shrinkable sleeve rests firmly against the outer surface of the object.

6. The medication device as set forth in claim 1, wherein the shrinkable sleeve is shrinkable from an initial state to a smaller, final state in response to a stimulus selected from a group consisting of a heat stimulus, a light stimulus and a chemical stimulus.

7. The medication device as set forth in claim 1, wherein the shrinkable sleeve includes a material that shrinks through an effect of heat, chemicals, or light.

8. The medication device as set forth in claim 1, wherein the shrinkable sleeve is configured to comprise a first radius in a first state and to comprise a second radius in a second state wherein the first radius is larger than the second radius.

9. The medication device as set forth in claim 1, wherein the shrinkable sleeve holds one of the first antenna and the second antenna in a desired position.

10. A method of assembling the medication device of claim 1, the method comprising:
    placing the shrinkable sleeve around the object when the shrinkable sleeve has a first diameter; and
    applying a stimulus to the shrinkable sleeve to reduce the shrinkable sleeve to a second diameter, the second diameter being smaller than the first diameter, such that the shrinkable sleeve rests firmly on the outer surface of the object and mounts at least one of the first antenna and the second antenna to the object.

11. A medication device comprising:
a cartridge or a syringe having a longitudinal axis and containing a medicament;
a housing receiving the cartridge or the syringe and having a center axis; and
an RFID device including:
at least one RFID chip with a first antenna, and
at least one RFID readout unit with a second antenna, the at least one RFID chip associated with one of the cartridge or the syringe and the housing and the at least one RFID readout unit associated with the other of the cartridge or the syringe and the housing, the first antenna of the at least one RFID chip and the second antenna of the at least one RFID readout unit each embodied as a coil independently extending completely around the longitudinal axis or the center axis and aligned so as to be coaxial with one another and with the longitudinal axis as well as with the center axis,
wherein at least one of the first antenna and the second antenna is integrated into a wall of one of the syringe, the cartridge, a shrinkable sleeve, and the housing.

12. The medication device of claim 11, wherein the shrinkable sleeve mounts at least one of the first antenna and the second antenna to the medication device.

13. The medication device as set forth in claim 12, wherein the shrinkable sleeve has been heated so that an inside diameter of the shrinkable sleeve mounts the first antenna or the second antenna on one of the cartridge or the syringe and the housing.

14. The medication device as set forth in claim 13, wherein the at least one of the first antenna and the second antenna is integrated into the shrinkable sleeve and the shrinkable sleeve tightly enwraps one of the cartridge or the syringe and the housing.

15. The medication device as set forth in claim 13, wherein the shrinkable sleeve includes a material that shrinks through an effect of heat, chemicals, or light.

16. The medication device as set forth in claim 13, wherein the shrinkable sleeve is configured to comprise a first radius in a first state and to comprise a second radius in a second state wherein the first radius is larger than the second radius.

17. The medication device as set forth in claim 11, wherein the housing is a part of a pen by which the medicament contained in the cartridge or the syringe can be administered.

18. The medication device as set forth in claim 11, wherein the at least one RFID chip contains information about the medicament contained in the cartridge or the syringe and/or about a route of administration of the medicament.

19. The medication device as set forth in claim 11, wherein the medication device is a pen.

20. The medication device as set forth in claim 11, wherein the shrinkable sleeve is shrinkable from an initial state to a smaller, final state in response to a stimulus selected from a group consisting of a heat stimulus, a light stimulus and a chemical stimulus.

21. The medication device as set forth in claim 20, wherein the shrinkable sleeve rests firmly against an outer surface of one of the cartridge or the syringe and the housing and is held in a desired position.

22. The medication device as set forth in claim 11, wherein the shrinkable sleeve integrates the at least one of the first antenna and the second antenna into one of the cartridge, the syringe, or the housing, wherein the shrinkable sleeve rests firmly on an outer surface of the cartridge, the syringe, or the housing.

23. A method of assembling a medication device, the medication device including a cartridge or a syringe with a longitudinal axis, a housing receiving the cartridge or the syringe and having a center axis, and an RFID device including at least one RFID chip with a first antenna, and at least one RFID readout unit with a second antenna, the at least one RFID chip associated with one of the cartridge or the syringe and the housing and the at least one RFID readout unit associated with the other of the cartridge or the syringe and the housing, the first antenna of the at least one RFID chip and the second antenna of the at least one RFID readout unit each embodied as a coil independently extending completely around the longitudinal axis or the center axis and aligned so as to be coaxial with one another and with the longitudinal axis as well as with the center axis, the method comprising:
placing a shrinkable sleeve around an object selected from a group consisting of: (1) the cartridge or the syringe; and (2) the housing when the shrinkable sleeve has a first diameter; and
applying a stimulus to the shrinkable sleeve to reduce the shrinkable sleeve to a second diameter, the second diameter being smaller than the first diameter, such that the shrinkable sleeve rests firmly on an outer surface of the object and mounts at least one of the first antenna and the second antenna to the object.

* * * * *